United States Patent [19]
Hobbs et al.

[11] Patent Number: 5,994,266
[45] Date of Patent: *Nov. 30, 1999

[54] ULTRA VIOLET RADIATION LIGNIN PROTECTED PESTICIDAL COMPOSITIONS

[75] Inventors: David G. Hobbs, Research Triangle Park, N.C.; Brian J. Campbell, Seattle, Wash.; William D. Lidster, Sacramento, Calif.

[73] Assignee: Abott Laboratories, Abbott Park, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/734,907

[22] Filed: Oct. 22, 1996

Related U.S. Application Data

[60] Provisional application No. 60/007,011, Oct. 25, 1995.

[51] Int. Cl.$^6$ .............................. A01N 25/10; A01N 25/22
[52] U.S. Cl. .......................... 504/116; 424/408; 514/777; 514/972
[58] Field of Search .............................. 504/116; 424/408; 514/777, 972

[56] References Cited

U.S. PATENT DOCUMENTS

| | | | |
|---|---|---|---|
| 3,813,235 | 5/1997 | Allan | 71/94 |
| 3,929,453 | 12/1975 | Dimitri et al. | 71/101 |
| 4,184,866 | 1/1980 | Dellicolli et al. | 71/65 |
| 4,244,728 | 1/1981 | DelliColli et al. | 71/65 |
| 5,552,149 | 9/1996 | Lebo, Jr. et al. | 424/408 |

FOREIGN PATENT DOCUMENTS

| | | | |
|---|---|---|---|
| 0592880 | 4/1994 | European Pat. Off. | A01N 47/30 |
| 0653158 | 5/1995 | European Pat. Off. | A01N 25/28 |
| 0669079 | 8/1995 | European Pat. Off. | A01N 25/14 |
| 2757379 | 6/1978 | Germany | A01N 9/36 |
| 19503157 | 8/1995 | Germany | A01N 25/26 |
| 9219102 | 11/1992 | WIPO | A01N 25/28 |
| 9505077 | 2/1995 | WIPO | A01N 25/12 |
| 9522253 | 8/1995 | WIPO | A01N 25/22 |
| 9533378 | 12/1995 | WIPO | A01N 25/26 |

OTHER PUBLICATIONS

Database WPI, Section Ch, Week 9615, Derwent Publications Ltd., JP 08 034 702A (Nissan Chem Ind. Ltd.), Jun. 2, 1995.

*Primary Examiner*—S. Mark Clardy
*Attorney, Agent, or Firm*—Michael J. Ward; Dugal S. Sickert

[57] ABSTRACT

The present invention relates to pesticidal compositions comprising an amount of a UV sensitive pesticide and a lignin as a UV sunscreen in an effective amount to protect the pesticide against inactivation by UV radiation for extending the persistence of the UV sensitive pesticide in the natural environment to control a pest and/or for reducing the amount of the pesticide typically needed to be a commercially effective pesticide. The present invention also relates to a method for protecting a UV sensitive pesticide against inactivation by UV radiation. The present invention further relates to a method for controlling a pest comprising exposing the pest to the pesticidal compositions of the present invention.

32 Claims, 2 Drawing Sheets

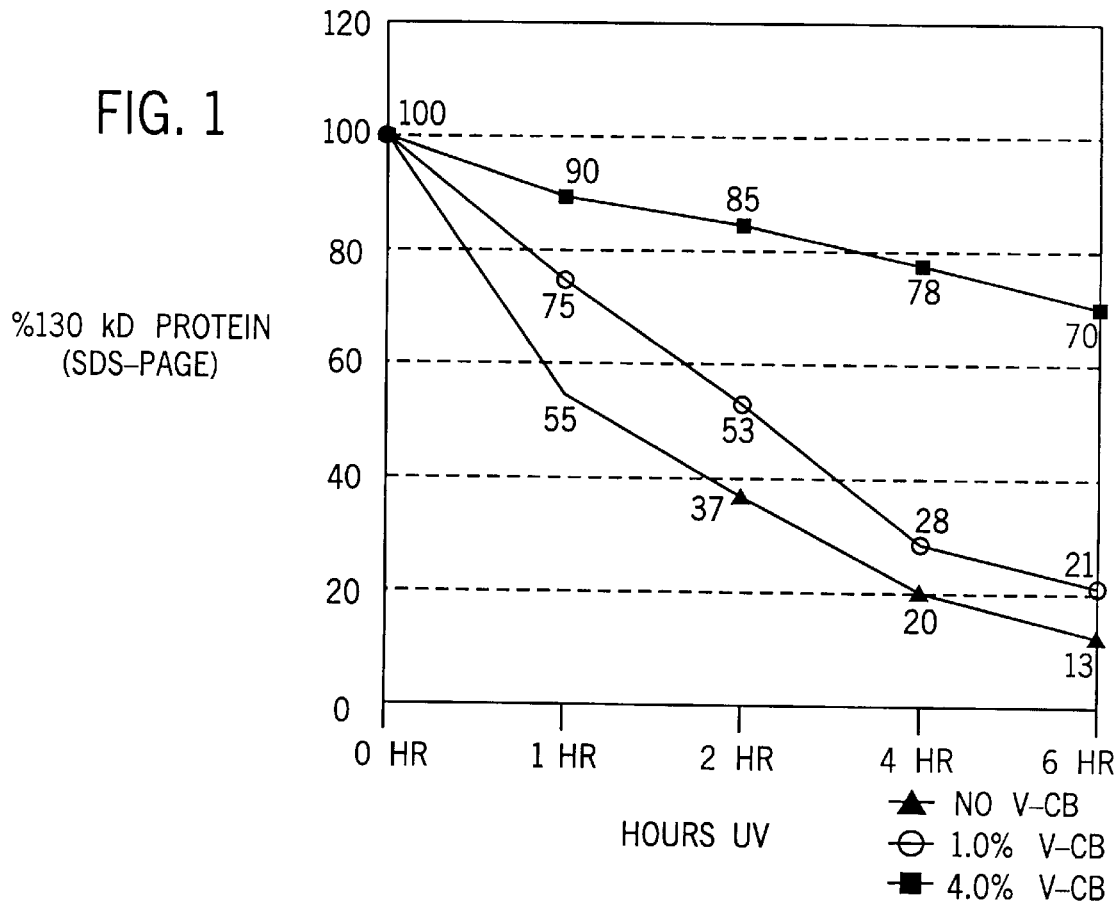

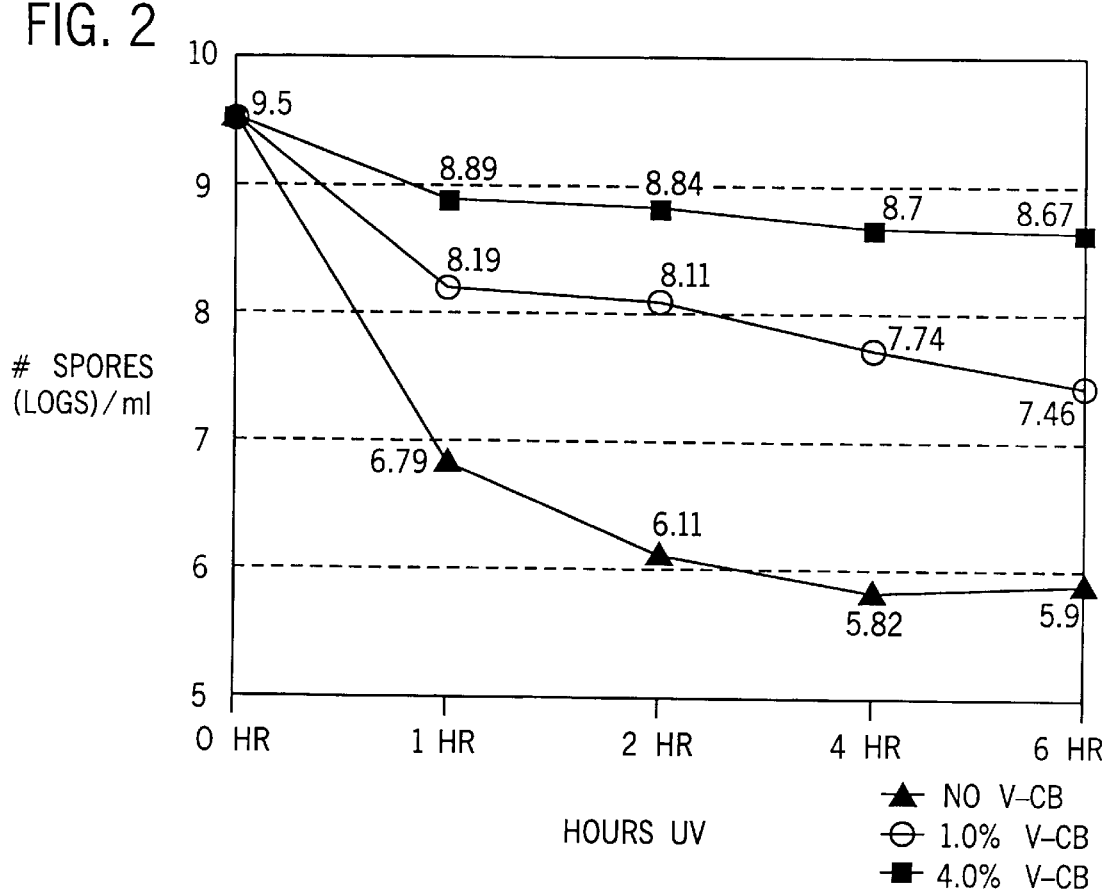

ULTRA VIOLET RADIATION LIGNIN PROTECTED PESTICIDAL COMPOSITIONS

This application claims the benefit of U.S. Provisional Application No. 60/007,011 filed Oct. 25, 1995.

BACKGROUND OF THE INVENTION

1. Field of the Invention

The present invention relates to pesticidal compositions comprising a UV sensitive pesticide and a UV sunscreen, wherein the UV sunscreen protects the pesticide against inactivation by UV radiation. The present invention also relates to a method for protecting a UV sensitive pesticide against inactivation by UV radiation. The present invention further relates to methods for using the pesticidal compositions to control a pest.

2. Description of the Related Art

The efficacy of a pesticide against a target pest depends on the persistence of the pesticide in the environment. A number of factors, particularly environmental factors, are detrimental to a pesticide. One of the most important environmental factors is ultraviolet (UV) radiation. UV radiation may inactivate a pesticide if it possesses an absorption maximum in the range 300–380 nm.

For example, biopesticides including *Bacillus thuringiensis* crystal delta-endotoxins and spores, entomopathogenic viruses, entomopathogenic fungi, and nematodes are particularly subject to inactivation by UV radiation. Furthermore, some chemical pesticides including insecticides, fungicides, herbicides, rodenticides, molluscicides, miticides, ovicides, algicides, larvicides, bactericides, and nematocides are also sensitive to UV radiation depending on the chemical structure of the particular chemical pesticide.

The art has strived to protect pesticides against UV radiation in order to economically provide a pesticidal formulation with extended environmental persistence and thus improved efficacy as a pesticide. Efforts have been directed to protecting pesticides by combining the pesticide with a UV sunscreen that protects the pesticide against inactivation by UV radiation and preserves the pesticidal activity.

An example of UV sunscreens is lignin (Pogwaite and Shapiro, in Samsonm Vlak, and Peters (eds.), *Proceedings, Fundamental and Applied Aspects of Invertebrate Pathology*, Foundation of the Fourth International Colloquium of Invertebrate Pathology, Wageningen, The Netherlands, 1986). Martignoni and Iwai disclose that sodium lignosulphonate is useful as a UV protectant for *Orgyia pseudotsugata* NPV (1985, *Journal of Economic Entomology* 78:982–987). Allan discloses a method for controlling the release of pesticides using a lignin polymer by chemical covalent bonding of a pesticide to a lignin polymeric substrate (U.S. Pat. No. 3,813,236). Dimitri and Falkehag also disclose the physical bonding of a lignin polymer and a pesticide to form a controlled release system (U.S. Pat. No. 3,929,453). DelliColli et al. disclose the use of cross-linked lignin gels as pesticidal carriers in controlled release pesticide systems (U.S. Pat. Nos. 4,184,866 and 4,244,728). Moss and Lim also disclose a process for encapsulating a pesticidal agent in lignin (WO 92/19102). Lebo and Detroit further disclose a method to provide resistance of agriculturally active substances to UV degradation by microencapsulating the active substances in a lignosulphonate covalently linked to a protein (EP 0 653 158 A1).

Lignin is a principal constituent of the woody structure of higher plants. Lignin products include, for example, lignosulphonates, alkali lignins, and oxylignins which may be obtained from sulphite, sulphate, and alkali waste liquors (Snook, 1982, *Handbook for Pulp & Paper Technologists*, TAPPI, Atlanta). The properties of lignin products vary significantly with regard to temperature limit for stability (e.g., less than 95° C. to less than 230° C.); salt tolerance (e.g., less than 0.1% precipitate in a salt solution containing sodium chloride, magnesium chloride, and calcium chloride with concentrations of less than 70 ppm to less than 270 ppm total dissolved solids); surface tension (e.g., 45 to 65 dynes/cm for a 1% aqueous solution); molecular size (e.g., less than 20,000 to less than 100,000 based on a standard lignosulphonate having an average molecular weight of 34,000); sulphonic sulphur (e.g., less than 2.0% to less than 9.5% sulphonic sulphur expressed as % S on solids); pH (e.g., a pH from about 3.5 to about 11.0); reducing groups (e.g., 0 to about 22); and cation (e.g., Na, Ca, Mg, $NH_3$, or Fe). The properties of some lignin products are described in the Borregaard Lignotech Bulletin entitled *Specialty Chemicals for Pesticide Formulations*.

While lignins have reportedly provided good results regarding the protection of pesticides against UV radiation, the results have not as yet made it possible to resolve critical problems necessary for obtaining commercially useful compositions which can be used in the field. Moreover, the art has not been able to identify the properties of a lignin material which provide commercially suitable protection of a pesticide against inactivation by UV radiation under field conditions.

It is an object of the present invention to provide pesticidal compositions with improved protection against UV radiation.

SUMMARY OF THE INVENTION

The present invention relates to pesticidal compositions, comprising (a) an amount of a UV sensitive pesticide and (b) a lignin in an effective amount to protect the pesticide against inactivation by UV radiation, wherein the lignin has the following properties:

(a) a surface tension of 50–54 dynes/cm (1% aqueous solution);

(b) a molecular size of less than 20,000;

(c) less than 2.0% sulphonic sulphur as % S on solids; and (d) 0% reducing sugars.

The present invention also relates to a method for protecting a UV sensitive pesticide against inactivation by UV radiation and a method for controlling a pest comprising applying to the pest the pesticidal compositions of the present invention.

BRIEF DESCRIPTION OF THE FIGURES

FIG. 1 illustrates the effect of UV radiation on *Bacillus thuringiensis* subsp. *kurstaki* delta-endotoxin in the presence and absence of a lignin of the present invention.

FIG. 2 illustrates the effect of UV radiation on *Bacillus thuringiensis* subsp. *kurstaki* spores in the presence and absence of a lignin of the present invention.

DETAILED DESCRIPTION OF THE INVENTION

The present invention relates to pesticidal compositions comprising an amount of a UV sensitive pesticide and a lignin as a UV sunscreen to protect the pesticide against inactivation by UV radiation.

The lignin of the invention may be any lignin such as lignosulphonates and salts thereof (e.g., Na, K, Ca, NH$_3$, and Mg salts), oxylignins and salts thereof, lignin liquors, Kraft lignins and derivatives thereof, and low or high molecular weight lignins having the specific properties defined above for the practice of the present invention.

Preferably, the lignin of the present invention further has a temperature stability of up to 120° C. and/or a salt tolerance of up to 70 ppm. In another preferred embodiment, a lignin of the present invention is in the form of a salt including, but not limited to, Na, K, Ca, NH$_3$, Mg, and Fe, preferably Na. The lignin of the present invention may be treated or untreated spent sulfite liquors obtained from the conversion of wood as the sulfite waste pulping liquor. They may be used as a whole liquor or as a purified material wherein the saccharide and/or inorganic constituents have been partially or wholly removed. In the practice of the present invention, the lignin is preferably utilized in a form that is not complexed, crosslinked, or covalently bound to the pesticide. The lignin of the present invention may be obtained from Borregaard Chemical Corporation under the trade names VANISPERSE™ CB (oxylignin) and MARASPERSE™ CBA-1 (sodium lignosulphonate). The properties of VANISPERSE™ CB and MARASPERSE™ CBA-1 as well as other lignin products are described in the Borregaard Lignotech Bulletin entitled *Specialty Chemicals for Pesticide Formulations*. The lignin products obtained from the various waste liquors may be chemically modified (for example, etherified, esterified, alkylated, halogenated, nitrated, mercurated, and hydrogenated) using methods known in the art.

The lignin is present in the pesticidal compositions of the invention in an effective amount to protect the pesticide against inactivation by UV radiation. Effective amount is defined herein as the amount of a lignin of the present invention sufficient to protect the pesticidal activity of a pesticide against UV radiation by about 20%, preferably by about 40%, more preferably by about 60%, and most preferably by about 100%. For example, the lignin is present in an amount between about 0.001% and about 10% of the volume applied to a given target pest, preferably between about 0.005% and about 8% more preferably between about 0.01% and about 6%, even more preferably between about 0.02% and about 4%, and most preferably between about 0.05% and about 2%. In a further example, the lignin is added to a formulation in an amount between about 1% and about 18% of the weight or volume of the formulation, preferably between about 1% and about 15%, more preferably between about 1% and about 12%, even more preferably between about 1% and about 10%, and most preferably between about 1% and about 5%. The amount of the lignin needed to protect a pesticide against UV radiation may vary significantly depending on the purity or the nature of the lignin preparation. The exact ratios of the lignin to the pesticide will depend on the concentration of the active ingredient of the pesticide in the composition, the level of active ingredient of the pesticide applied per unit area, and the volume of tank mix applied per unit area. Depending on the recommended use rate for a pesticide formulated product, the lignin may be combined either with the pesticide product in a tank mix or in the formulated product In either case, the effective concentration of the lignin for protecting the pesticide against UV radiation will be the same.

"Pesticidal activity" is defined herein as a measure of the amount of activity of a pesticide against a pest through killing or stunting of the growth of the pest or protecting a plant from pest infestation. The pesticidal activity of a pesticide may be assayed using procedures known in the art, such as artificial diet incorporation, artificial diet overlay, leaf painting, leaf dip, and foliar spray.

The pesticide in the pesticidal compositions of the present invention may be a biopesticide, insecticide, fungicide, herbicide, rodenticide, molluscicide, miticide, ovicide, algicide, larvicide, bactericide, or nematocide. Preferably, the pesticide is a biopesticide, e.g., a biopesticide obtained from a Bacillus strain. In a more preferred embodiment, the pesticide is obtained from a *Bacillus thuringiensis* strain. The *Bacillus thuringiensis* pesticide in the pesticidal compositions of the present invention may be derived from, but not limited to, *Bacillus thuringiensis* subsp. *aizawai*, *Bacillus thuringiensis* subsp. *alesh*, *Bacillus thuringiensis* subsp. *canadiensis*, *Bacillus thuringiensis* subsp. *colmeri*, *Bacillus thuringiensis* subsp. *coreanensis*, *Bacillus thuringiensis* subsp. *dakota*, *Bacillus thuringiensis* subsp. *darmstadiensis*, *Bacillus thuringiensis* subsp. *dendrolimus*, *Bacillus thuringiensis* subsp. *entomocidus*, *Bacillus thuringiensis* subsp. *finihmus*, *Bacillus thuringiensis* subsp. *galleriae*, *Bacillus thuringiensis* subsp. *indiana*, *Bacillus thuringiensis* subsp. *israelensis*, *Bacillus thuringiensis* subsp. *kenyae*, *Bacillus thuringiensis* subsp. *kurnamotoensis*, *Bacillus thuringiensis* subsp. *kurstaki*, *Bacillus thuringiensis* subsp. *kyushuensis*, *Bacillus thuringiensis* subsp. *japonensis*, *Bacillus thuringiensis* subsp. *mexcanensis*, *Bacillus thuringiensis* subsp. *morrisoni*, *Bacillus thuringiensis* subsp. *neoleonensis*, *Bacillus thuringiensis* subsp. *nigeriae*, *Bacillus thuringiensis* subsp. *ostriniae*, *Bacillus thuringiensis* subsp. *pakistani*, *Bacillus thuringiensis* subsp. *pondicheriensis*, *Bacillus thuringiensis* subsp. *shandongiensis*, *Bacillus thuringiensis* subsp. *silo*, *Bacillus thuringiensis* subsp. *sotto*, *Bacillus thuringiensis* subsp. *subtoxicus*, *Bacillus thuringiensis* subsp. *tenebrionis*, *Bacillus thuringiensis* subsp. *thompsoni*, *Bacillus thuringiensis* subsp. *tochigiensis*, *Bacillus thuringiensis* subsp. *tohokuensis*, *Bacillus thuringiensis* subsp. *tolworthi*, *Bacillus thuringiensis* subsp. *toumranoffi*, *Bacillus thuringiensis* subsp. *wuhanensis*, or *Bacillus thuringiensis* subsp. *yunnanensis*. In a most preferred embodiment, the pesticide is derived from a *Bacillus thuringiensis* subsp. *kurstaki* strain. In another most preferred embodiment, the pesticide is derived from a *Bacillus thuringiensis* subsp. *aizawai* strain.

The *Bacillus thuringiensis* pesticide in the pesticidal compositions of the present invention may also be derived from a cell wherein a gene, which encodes a *Bacillus thuringiensis* delta-endotoxin or a pesticidally-active fragment thereof, has been inserted. Further within the scope of the present invention, the *Bacillus thuringiensis* pesticide may be derived from a transconjugate strain wherein a plasmid containing a gene, which encodes a *Bacillus thuringiensis* delta-endotoxin or a pesticidally-active fragment thereof, has been transferred by cell-cell conjugation.

The *Bacillus thuringiensis* pesticide, i.e., a delta-endotoxin or a pesticidally-active fragment thereof, may be selected from the group including, but, not limited to, CryI, CryII, CryIII, CryIV, CryV, and CryVI. More specifically, the *Bacillus thuringiensis* delta-endotoxin or the pesticidally-active fragment thereof may include, but is not limited to, CryIA(a), CryIA(b), CryIA(c), CryIB, CryIC, CryID, CryIE, CryIF, CryIIA, CryIIB, CryIIIA, CryIIIB, CryIIIC, CryIVA, CryIVB, CryIVC, CryIVD, CryV, CryVI, and CytA. In a preferred embodiment, the *Bacillus thuringiensis* delta-endotoxin is CryIA. In a more preferred embodiment, the delta-endotoxin is CryIA(a), CryIA(b), or CryIA(c). In another preferred embodiment, the *Bacillus thuringiensis* delta-endotoxin is CryIC.

It is also within the scope of the present invention that the pesticide may be a spore derived from a Bacillus strain. In another preferred embodiment, the Bacillus pesticide is a Bacillus spore. In a more preferred embodiment, the Bacillus pesticide is a *Bacillus thuringiensis* spore.

The pesticide of the present invention may also be a pesticidal metabolite derived from a microorganism, preferably a Bacillus strain, more preferably a *Bacillus thuringiensis* strain, wherein the pesticidal metabolite is subject to inactivation by UV radiation.

The pesticide of the present invention may also be an entomopathogenic virus. Examples of such entomopathogenic viruses include, but are not limited to, *Autographa californica* nuclear polyhedrosis virus (NPV), *Syngrapha falcifera NPV, Cydia pomonella* granulosis virus (GV), *Helicoverpa zea NPV, Heliothis zea NPV, Lyntantria dispar NPV, Orgyia pseudotsugata NPV, Spodoptera exigua NPV, Neodiprion lecontei NPV, Neodiprion sertifer NPV, Harrisina brillians NPV, Anticarsia gemmatalis NPV*, and *Endopiza viteana* Clemens NPV.

The pesticide of the present invention may further be an entomopathogenic fungus. Examples of such entomopathogenic fungi include, but are not limited to, *Erynia neoaphidis, Neozygites fresenii* (Nowakowski), *Beauveria bassiana, Metarhiziurn anisopliae*, and *Verticillium lecanii.*

The pesticide of the present invention also may be a chemical pesticide, e.g., an insecticide, a fungicide, a herbicide, a rodenticide, a molluscicide, a miticide, an ovicide, an algicide, a larvicide, a bactericide, and a nematocide. Examples of such chemical insecticides include, but are not limited to, insect growth regulators, carbamates, organophosphates, pyrethroids, inorganic fluorines, pyrazoles, and pyrroles.

The pesticidal compositions of the present invention may also comprise one or more synergizers, potentiators, or phagostimulants known in the art. For example, the potentiator disclosed in WO 94/09630 or a pesticidally-active salt thereof may be used in the compositions of the present invention.

The pesticidal compositions of the present invention may further comprise a deposition agent which assists in preventing the composition from drifting from the target area during application (e.g., as it is sprayed from a plane), or from being blown away from the plant once it has been deposited. The deposition agent in the compositions of the present invention is preferably a proteinaceous material, which has the added benefit of being palatable to the insect. Any animal or vegetable protein is suitable for this purpose, in dry or in liquid form. Examples of useful sources of protein which can be conveniently and economically added to the composition include, but are not limited to, soy protein, potato protein, soy flour, potato flour, fish meal, bone meal, yeast extract, and blood meal. Alternative deposition agents include modified cellulose (carboxymethylcellulose), botanicals (grain flours, ground plant parts), non-phyllosilites (talc, vermiculite, diatomaceous earth), natural clays (attapulgite, bentonite, kaolinite, montmorillonite), and synthetic clays (Laponite). When utilized, the deposition agent is present in the pesticidal compositions of the present invention in an amount of between about 0.4% w/w and about 50% w/w, preferably between about 1% w/w and about 20% w/w.

The pesticidal compositions of the present invention may further comprise an antifreeze/humectant agent which suppresses the freeze point of the product and helps minimize evaporation when sprayed and which maintains deposit texture making the product more efficacious and palatable. The antifreeze/humectant agent in the compositions of the present invention is selected from the group consisting of an alcohol, a sugar alcohol, ethylene glycol, propylene glycol, dipropylene glycol, glycerol, butylene glycols, pentylene glycols and hexylene glycols. When utilized, the antifreeze/humectant agent is present in the pesticidal compositions of the present invention in an amount of between about 0.5% w/w and about 25% w/w, preferably between about 2% w/w and about 15% w/w.

The pesticidal compositions of the present invention may further comprise a surfactant in an amount where it acts as an emulsifying, a wetting, or a dispersing agent. Examples of such surfactants are anionic surfactants such as carboxylates, for example, a metal carboxylate of a long chain fatty acid; N-acylsarcosinates; mono or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g., butyl-naphthalene sulphonate; salts or sulphonated naphthalene-formaldehyde condensates; salts of sulphonated phenol-formaldehyde condensates; or more complex sulphonates such as amide sulphonates, e.g., the sulphonated condensation product of oleic acid and N-methyl taurine or the dialkyl sulphosuccinates, e.g., the sodium sulphonate or dioctyl succinate. Further examples of such surfactants are nonionic surfactants such as condensation products of fatty acid esters, fatty alcohols, fatty acid amides or fatty-alkyl- or alkenyl-substituted phenols with ethylene oxide, block copolymers of ethylene oxide and propylene oxide, acetylenic glycols such as 2,4,7,9-tetraethyl-5 decyn4,7-diol, or ethoxylated acetylenic glycols. Further examples of such surfactants are cationic surfactants such as aliphatic mono-, di-, or polyamines such as acelates, naphthenates or oleates; oxygen-containing amines such as an amine oxide of polyoxyethylene alkylamine; amide-linked amines prepared by the condensation of a carboxylic acid with a di- or polyamine; or quaternary ammonium salts. When utilized, the surfactant is present in an amount of between about 0.5% w/w and about 25% w/w, preferably between about 1% w/w and about 8% w/w.

The pesticidal compositions of the present invention may further comprise an inert material. Examples of inert materials include inorganic minerals such as diatomaceous earth, kaolin, mica, gypsum, fertilizer, phyllosilicates, carbonates, sulfates, or phosphates; organic materials such as sugars, starches, or cyclodextrins; or botanical materials such as wood products, cork, powdered corncobs, rice hulls, peanut hulls, and walnut shells.

The pesticidal compositions according to the present invention may further comprise a preservative, a feeding stimulant, an attractant, an encapsulating pesticide, a binder, a dye, a buffer, a flow agent, or other component to facilitate product handling and application for particular target pests.

The present invention also relates to a method for protecting a UV sensitive pesticide against inactivation by UV radiation comprising treating the pesticide with a lignin of the present invention.

The amount of a pesticide needed to achieve commercially acceptable control of a pest will differ from one pesticide to another pesticide, and furthermore, will vary depending on the pest and the crop. The efficacy of a large number of pesticides is well established in the art. The amounts required for commercial utility are either known or are easily determined by one of ordinary skill in the art.

A pesticide alone, at certain levels, may provide commercially acceptable control of a pest. However, the amount of any given pesticide required to achieve commercially acceptable control may be quite high, and, therefore, impractical economically. In accordance with the present invention, the amount of a pesticide required in any given composition may be reduced by combining the pesticide with an effective amount of a lignin of the present invention to protect the pesticide against the inactivating effect of UV radiation, and thereby to extend the persistence of the pesticide in the environment and to increase the efficacy of the pesticide in controlling a pest under field conditions.

Less pesticide may be needed in a composition containing a lignin of the present invention as a UV sunscreen to achieve the same efficacy compared to a composition not containing a lignin. This further benefit of the present invention may be achieved by determining the amount of a UV sensitive pesticide required alone to achieve commercially acceptable control of a pest. The amount of a lignin needed to provide the benefit of reducing the amount of the UV sensitive pesticide used commercially can be determined, for example, by taking the amount of the pesticide required to achieve commercially acceptable control of a pest and progressively reducing that amount of the pesticide, e.g., 20%, and progressively adding the lignin in increasing amounts until the level of control of the pest equals that which is achieved with the pesticide alone in amounts typically used commercially.

Likewise, the combination of a UV sensitive pesticide and a lignin may be useful in bringing about the commercial use of a UV sensitive pesticide which alone would have been commercially impractical or commercially ineffective as a pesticide.

The present invention is further directed to a method for controlling pest infestation on plants comprising applying to a plant pesticidal compositions of the present invention.

The pesticidal compositions of the present invention can be applied in a dry or liquid form, e.g., a suspension, a solution, an emulsion, a dusting powder, a dispersible granule, a wettable powder, an emulsifiable concentrate, an aerosol or impregnated granule, or a concentrate or primary composition which requires dilution with a suitable quantity of water or other diluent before application. The concentrations of each component in the composition will vary depending on the pesticide and mode of application. The pesticide concentration will vary depending upon the nature of the particular composition, specifically, whether it is a concentrate or to be used directly. The composition may contain about 1% to about 98% of a solid or liquid inert carrier, about 1% to about 30% of a pesticide. The compositions will be preferably administered at the labeled rate for the commercial product, preferably about 0.01 pound to 5.0 pounds per acre when in dry form and at about 0.01 pint to 25 pints per acre when in liquid form.

The pesticidal compositions of the present invention can be applied directly to a plant by, for example, spraying or dusting at the time when the pest has begun to appear on the plant or before the appearance of pests as a protective measure. The pesticidal compositions can be applied by foliar, furrow, broadcast granule, "lay-by", or soil drench application. The compositions of the present invention can also be applied directly to ponds, lakes, streams, rivers, still water, and other areas subject to infestation by pests of concern to public health. The compositions can be applied by spraying, dusting, sprinkling, or the like. The spray or dust can conveniently contain another pesticide. The pesticidal compositions of the present invention are preferably applied directly to the plant.

The pesticidal compositions of the present invention can be applied to protect a number of different plant types, including, but not limited to, cereals (wheat, barley, rye, oats, rice, sorghum and related crops), beets (sugar beet and fodder beet), drupes, pomes and soft fruit (apples, pears, plums, peaches, almonds, cherries, strawberries, raspberries, and blackberries), leguminous plants (alfalfa, beans, lentils, peas, soybeans), oil plants (rape, mustard, poppy, olives, sunflowers, coconuts, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages and other brassicae, carrots, onions, tomatoes, potatoes), lauraceae (avocados, cinnamon, camphor), deciduous trees and conifers (lindentrees, yew-trees, oak-trees, alders, poplars, birch-trees, firs, larches, pines), or plants such as maize, turf plants, tobacco, nuts, coffee, sugar cane, tea, vines, hops, bananas and natural rubber plants, as well as ornamentals.

A lignin of the present invention may be applied separately to a plant previously exposed to a UV sensitive pesticide.

The present invention further relates to a method for applying a lignin as a UV sunscreen to a transgenic plant, which contains a gene that encodes a *Bacillus thuringiensis* pesticide.

The pesticidal compositions of the present invention can be used in the treatment or prevention of infestations of a number of different insect types. It is particularly preferred to use the compositions of the present invention to eliminate pests of the order Lepidoptera, e.g., *Achroia grisella, Acleris gloverana, Acleris variana, Adoxophyes orana, Agrons ipsilon, Alabama argillacea, Alsophila pometaria, Amyelois transitella, Anagasta kuehniella, Anarsia lineatella, Anisota senatoria, Antheraea pernyi, Antlcarsia gemmatalis,* Archips sp., Argyrotaenia sp., *Athetis mindara, Bombyx mori, Bucculatrix thurberiella, Cadra cautella,* Choristoneura sp., *Cochylis hospes, Colias eurytheme, Corcyra cephalonica, Cydia latiferreanus, Cydia pomonella, Datana integerrima, Dendrolimus sibericus, Desmia funeralis, Diaphania hyalinata, Diaphania nittdalis, Diatraea grandiosella, Diatraea saccharalis, Ennomos subsignaria, Eoreuma loftini, Ephesna elutella, Erannis tiliaria, Estigmene acrea, Eulia salubricola, Eupoecilia ambiguella, Euproctis chrysorrhoea, Euxoa messoria, Galleria mellonella, Grapholita molesta, Harrisina americana, Helicoverpa subflexa, Helicoverpa zea, Heliothis virescens, Hemileuca oliviae, Homoeosoma electellum, Hyphantria cunea, Keiferia lycopersicella, Lambdina iscellaria fiscellaria, Lambdina fscellaria lugubrosa, Leucoma salicis, Lobesia botrana, Loxostege sticticalis, Lymantria dispar, Macalla thyrsisalis,* Malacosoma sp., *Mamestra brassicae, Mamestra configurata, Manduca quinquemaculata, Manduca sexta, Maruca testulalis, Melanchra picta, Operophtera brumata,* Orgyia sp., *Ostrinia nubilalis, Paleacrita vernata, Papilio cresphontes, Pectinophora gossypiella, Phryganidia californica, Phyllonorycter blancardella, Pieris napi, Pieris rapae, Plathypena scabra, Platynota flouendana, Platynota sultana, Platyptilia carduidactyla, Plodia interpunctella, Plutella xylostella, Pontia protodice, Pseudaletia unipluncta, Pseudoplusia includens, Sabulodes aegrotata, Schizura concinna,*

Sitotroga cerealella, Spilonota ocellana, Spodoptera sp., Thaurnstopoea pityocampa, Tineola bisselliella, Trichoplusia ni, Udea rubigalis, Xylomyges curialis, and Yponomeuta padella; the order Coleoptera, e.g., Leptinotarsa sp., Acanthoscelides obtectus, Callosobruchus chinensis, Epilachna varivestis, Pyrrhalta luteola, Cylas formicarius elegantulus, Listronotus oregonensis*, Sitophilus sp., *Cyclocephala borealis, Cyclocephala immaculata, Macrodactylus subspinosus, Popillia japonica, Rhizotrogus majalis, Alphitobius diaperinus, Palorus ratzeburgi, Tenebrio molitor, Tenebrio obscurus, Tribolium castaneum, Tribolium confusum*, and *Tribolius destructor*, the order Diptera, e.g., Aedes sp., *Andes vittatus, Anastrepha ludens,, Anastrepha suspensa, Anopheles barberi, Anopheles quadrimaculatus, Armigeres subalbatus, Calliphora stygian, Calliphora vicina, Ceratitis capitata, Chironomus tentans, Chrysomya rufifacies, Cochliomyia macellaria*, Culex sp., *Culiseta inornata, Dacus oleae, Delia antiqua, Delia platura, Delia radicum, Drosophila melanogaster, Eupeodes corollae, Glossina austeni, Glossina brevipalpis, Glossina fuscipes, Glossina morsitans centralis, Glossina morsitans morsitans, Glossina moristans submorsitans, Glossina pallidipes, Glossina palpalis gambiensis, Glossina palpalis palpalis, Glossina tachinoides, Haemagogus equinus, Haematobia irritans, Hypoderma bovis, Hypoderrna lineatum, Leucopis ninae, Lucilia cuprina, Lucilia sericata, Lutzomyia longlpaipis, Lutzomyia shannoni, Lycoriella mali, Mayetiola destructor, Musca autumnalis, Musca domestica*, Neobellieria sp., *Nephrotoma suturalis, Ophyra aenescens, Phaenicia sericata*, Phlebotomus sp., *Phormia regina, Sabethes cyaneus, Sarcophaga bullata, Scatophaga stercoraria, Stomoxvs calcitrans, Toxorhynchites amboinensis*, and *Tripteroides bambusa*; the order Acari, e.g., *Oligonychus pratensis, Panonychus ulmi*, and *Tetran chus urticae*; the order Hymenoptera, e.g., *Iridomyrmex humilis* and *Solenopsis invicta*; the order Isoptera, e.g., *Reticulitermes hesperus, Reticulitermes flavipes, Coptotermes forrnosanus, Zootermopsis angusticollis, Neotermes connexus, Incisiterrnes minor*, and *Incisitermes immigrans*; the order Siphonaptera, e.g., *Ceratophyllus gallinae, Ceratophyllus niger, Nosopsyllus fasciatus, Leptopsylla segnis, Ctenocephalides canis, Ctenocephalides felis, Echicnophaga gallinacea, Pulex irritans, Xenopsylla cheopis, Xenopsylla vexabilis*, and *Tunga penetrans*; and the order Tylenchida, e.g., *Melodidogyne incognita* and *Pratylenchus penetrans.*

The present invention is further described by the following examples which should not be construed as limiting the scope of the invention.

EXAMPLES

Example 1

Strains and Materials

*Bacillus thuringiensis* subsp. *kurstaki* (NRRL B-21147) is obtained from the Northern Regional Research Laboratory (NRRL), Peoria, Ill. BIOBIT™ FC and BIOBIT™ HPWP are obtained from Novo Nordisk A/S, Bagsvaerd, Denmark. DIPEL™ 2× WP is obtained from Abbott Laboratories, Inc., Chicago, Ill. AGREE™ WP is obtained from Ciba-Geigy Corporation, Greensboro, N.C. VANISPERSE-CB™, UFOXANE™ 3A, MARASPERSE™ CBA-1, and BORRESPERSE™ CA are obtained from Borregaard A/S, Sarpsborg, Norway. REAX™ 88B and POLYFON™ O are obtained from Westvaco Inc., Charleston, S.C. CARBOLAZE™ L is obtained from Chemlig International Industries Inc., Houston, Tex. UVINUL™ P25 is obtained from BASF, Lyngby, Denmark.

Example 2

Cultivation of *Bacillus thuringiensis* subsp. *kurstaki* NRRL B-21147

*Bacillus thuringiensis* subsp. *kurstaki* is cultivated for 72 hours at 30° C. in a medium with the following composition:

| | |
|---|---|
| Soy Protein | 40 g/liter |
| Maltodextrin | 40 g/liter |
| $MgSO_4$—$7H_2O$ | 0.3 g/liter |
| $KH_2PO_4$ | 1.8 g/liter |
| $K_2HPO_4$ | 4.5 g/liter |
| Trace Metals | 0.2 ml |

One portion of the whole broth preparation is centrifuged and spray dried to a potency of 75,000 IU per mg powder against third instar *Trichoplusia ni* larvae (HD-1-1980 standard, NRRL, Peoria, Ill.). Another portion of the whole broth is evaporated to a potency of 13,000 IU per ml against third instar *Trichoplusia ni* larvae.

Example 3

Petri Dish Bioassay General Procedure

The *Bacillus thuringiensis* subsp. *kurstaki* spray dried preparation from Example 2 is diluted with deionized water to a potency of approximately 500 IU per mg. A UV sunscreen to be tested is added to the diluted *Bacillus thuringiensis* preparation as % w/w and mixed. Eight grams of each mixture with a total potency of approximately $3.9\times10^6$ IU is added to a 6" diameter Petri dish, spread evenly across the surface, and dried down to a thin film at 40° C. for 2 hours or at room temperature overnight in a vacuum hood. The thickness of the dried film may vary slightly across the dish diameter.

The dish with the dried mixture is exposed to natural sunlight or to an artificial UV source. The time of exposure is typically 0 to 24 hours. The exposure time depends on the sunscreen tested and the source of the UV radiation. For the artificial UV source, a Westinghouse FS40 Fluorescent Sun-Lamp is used. The bulb has a UV max at about 310 nm with the major portion of its light emitted between 280 and 350 nm. The Petri dish is exposed for a period of time relative to that necessary to degrade the unprotected control, the nature of the test UV screen, the distance from the source of the UV radiation, and the source of the UV radiation. After exposure, the *Bacillus thuringiensis* subsp. *kurstaki* preparation in each Petri dish is resuspended with a rubber spatula in 32 g of deionized water to a potency of approximately 125 IU per mg. The resuspended solution is then homogenized for 30 seconds on a Silveson L4R Homogenizer at a setting of 3. The treatments and appropriate controls are then tested in a *Spodoptera exigua* egg-overlay assay as described below.

A 1 ml aliquot of the homogenized solution containing the *Bacillus thuringiensis* subsp. *kurstaki* preparation is added to 1 ml of egg agar with a final potency of approximately 62 IU per ml. Six 1:1 serial dilutions are prepared from the egg agar, *Bacillus thuringiensis* solution resulting in 6 doses per treatment. Fifty μl of each dose are added to wells in a plastic tray containing 0.5 ml of egg agar per well (20 wells per dose). A total of 3–5 *Spodoptera exigua* eggs are placed into each well. The trays are covered with a perforated sheet of Mylar and incubated for 7 days at 28° C. and 65% relative humidity. Each treatment is scored as % mortality of *Spodoptera exigua* after 7 days. For the unexposed control treatment, the most dilute dose (0.97 IU/ml) yields 0–5% mortality *Spodoptera exigua* while the most concentrated dose (31 IU/ml) yields usually 60–100% mortality *Spodoltera exigua*.

Example 4

Foliar Bioassay General Procedure

Whole broccoli plants are sprayed with a Devires Linear Track Sprayer Model SB6-032 equipped with a single hollow cone nozzle (Delavan HC-8 or TeeJet XS-2, depending on the application volume) at a distance of approximately 18 inches above the mean leaf height. The volume of spray as applied corresponds to 20 gallons per acre of surface area at a rate of 16 BIU of BIOBIT™ FC active ingredient per acre. After the spray deposit dries, the plants are placed under an artificial UV source (Westinghouse FS40 SunLamp) at an approximate distance of 12 inches mean leaf diameter height below the tubes. The leaves are exposed to the UV lamp source for 6 hours unless otherwise noted.

After six hours of exposure to the artificial UV source, the plants are removed and six leaves are excised from the treated plants for foliar bioassay determinations using a disc/cup method. For each bioassay, six 25 ml cups each containing a leaf disc and five *Spodoptera exigua* third instar larvae are incubated at 37° C. for three days in 65% relative humidity (n=30 per assay). The number-of dead larvae are recorded 3 days after treatment Bioassays are replicated 2–4 times, and the results are entered into the Pesticide Research Manager (PRM). Statistical differences are obtained using Duncan's Multiple Range Test applied in the summary of data in PRM.

Example 5

Comparison of Lignin Preparations—Petri Dish Bioassays

Lignin preparations (VANISPERSE-CB™, CARBOLAZE™ L, MARASPERSE™ CBA-1, UFOXANE™, BORRESPERSE-A™, REAX™ 88B, and POLYFON™ O) are compared as to their ability to protect the *Bacillus thuringiensis* subsp. *kurstaki* spray dried preparation of Example 2 against UV inactivation using the method described in Example 3 where the lignin preparation is present at 0.2% w/w of the volume applied and exposure to an artificial UV source is for 22 hours.

The results, as shown in Table I, demonstrate that VANISPERSE-CB™ and MARASPERSE™ CBA-1 are superior in their UV protection of the *Bacillus thuringiensis* subsp. *kurstaki* spray dried preparation.

TABLE I

| Sunscreen | Sunlamp % Remaining Activity |
|---|---|
| Control | 100% |
| No W Sunscreen | 33% |
| Oxylignin | |
| VANISPERSE-CB ™ | 80% |
| Lignosulphonate | |
| CARBOLAZE ™ L | 57% |
| MARASPERSE ™ CBA-1 | 86% |
| UFOXANE ™ | 59% |

TABLE I-continued

| Sunscreen | Sunlamp % Remaining Activity |
|---|---|
| BORRESPERSE ™ CA | 30% |
| Alkali Lignin | |
| REAX ™ 88B | 41% |
| POLYFON ™ O | 60% |

The study described above is repeated except the lignin preparations VANISPERSE-CB™, CARBOLAZE™ L, and MARASPERSE™ CBA-1 are tested at 0.05% w/w of the volume applied and exposure to an artificial UV source or to sunlight is for 4 hours.

The results as shown in Table II show that VANISPERSE-CB™ and MARASPERSE™ CBA-1 provide UV protection whether exposed to artificial sunlight or to natural sunlight.

TABLE II

| Sunscreen | Sunlamp % Remaining Activity | Sunlight % Remaining Activity |
|---|---|---|
| Control | 100% | 100% |
| No UV Sunscreen | 20% | 20% |
| VANISPERSE-CB ™ | 78% | 82% |
| CABOLAZE ™ L | 56% | 66% |
| MARASPERSE ™ CBA-1 | 71% | 71% |

Example 6

Effect of VANISPERSE-CB™ on Spores and Delta-Endotoxin of *Bacillus thuringiensis* subsp. *kurstaki*

VANISPERSE-CB™ is mixed with BIOBIT™ FC or the *Bacillus thuringiensis* subsp. *kurstaki* evaporated preparation as described in Example 2 at concentrations of 1% and 4% and pHs of 4.5 and 6.0. The samples are diluted to a tank mix dilution of approximately 1:20. A control without VANISPERSE-CB™ is also made. A 200 $\mu$l aliquot from each sample is placed onto a glass microscope slide and allowed to dry in a vacuum hood overnight. The slides are exposed to a UV sunlamp (Westinghouse FS40 SunLamp) at a distance of approximately 2 feet for 0, 1, 2, 4, and 6 hours. After exposure to the UV sunlamp, the samples are reconstituted in 1.0 ml of deionized water and concentrated to 50 $\mu$l using a Speed-Vac. The samples are sonicated for 5 seconds using a Brausonic Model 1510 Sonicator and run on SDS-PAGE minigels using a Pharmacia Phast System according to the manufacturer's instructions. The SDS-PAGE minigels are then scanned using a Pharmacia LKB ImageMaster DTS to determine the concentration of the 130 kDa protein.

For spore counts, the Speed-Vac concentrated samples from above are diluted 20-fold with deionized water in Eppendorf tubes. The tubes are placed on ice and sonicated for two 30 second intervals. A 0.25 ml aliquot of each sample is mixed with 0.75 ml of 0.1% TWEEN™ 20 and vortexed for 1–3 seconds. Each sample is then diluted 1:800 with 0.1% TWEEN™ 20. The 1:800 dilution of each sample is further diluted to 1:8,000, 1:80,000, 1:800,000, and 1:8,000,000 using 0.1% TWEEN™ 20 as the diluent and vortexing for 1–3 seconds after adding the diluent. A 100 $\mu$l aliquot of each dilution is spread onto a Petri plate consisting of Nutrient Broth medium. The plates are incubated at 28–30° C. overnight. The number of colonies on each plate are recorded and used to determine the number of spores per ml in the undiluted sample.

The results for the whole broth at pH 4.5 indicate that VANISPERSE-CB™ significantly reduced the inactivation of the delta-endotoxin according to SDS-PAGE analysis and the inactivation of the spores as shown in FIG. 1 and FIG. 2, respectively. The spore count at 0 hour is $4.6 \times 10^9$ spores per ml. In the absence of VANISPERSE-CB™, the spore count after 6 hours is $9 \times 10^5$, while in the presence of 1% and 4% VANISPERSE-CB™, the spore count is $4.6 \times 10^7$ and $6.7 \times 10^8$, respectively. According to SDS-PAGE analysis, the amount of 130 kDa delta-endotoxin remaining after 6 hours exposure to UV radiation in the presence of 1% VANISPERSE-CB™ is approximately 21% while in the presence of 4% VANISPERSE-CB™, is approximately 70%. The amount of 130 kDa delta-endotoxin remaining after 6 hours exposure to UV radiation in the absence of VANISPERSE-CB™ is approximately 13%.

Similar results are observed for the whole broth at pH 6.0 and BIOBIT™ FC at pH 4.5 and pH 6.0.

Example 7

Foliar Bioassays of BIOBIT™ FC with VANISPERSE-CB™

On a w/w basis, 94 parts of BIOBIT™ FC are blended with 6 parts of VANISPERSE-CB™ using a Brinkmann Heidolph Propeller Mixer Model 2101 until a homogenous suspension is achieved. The subsequent blend is diluted in water to 20 gallons. This dilution is then applied to whole broccoli plants using a track sprayer equipped with a single hollow cone nozzle (Delavan HC-8) and bioassayed as described in Example 4.

The results show that the percent mortality at 3 days after treatment is 17% for BIOBIT™ FC, 35% for BIOBIT™ FC+6% VANISPERSE-CB™, and 7% for the untreated control.

The procedure is repeated except the volume of spray applied corresponds to 5 gallons per acre of surface area instead of 20 gallons per acre.

The results demonstrate that the percent mortality at 3 days after treatment is 15% for BIOBIT™ FC, 84% for BIOBIT™ FC+6% VANISPERSE-CB™, and 7% for the untreated control.

Example 8

Foliar Bioassays of BIOBIT™ FC with CARBOLAZE™ L

The procedure described in Example 7 is repeated using CARBOLAZE™ L in place of VANISPERSE-CB™.

The results indicate that the percent mortality at 3 days after treatment is 17% for BIOBIT™ FC, 12% for BIOBIT™ FC+6% CARBOLAZE™ L, and 7% for the untreated control.

Example 9

Foliar Bioassays of BIOBIT™ FC with VANISPERSE-CB™ or CARBOLAZE™ L

The procedure described in Example 7 is repeated except 16 BIU is applied at a rate of 5 gallons per acre of surface area.

The results show that the percent mortality at 3 days after treatment is 15% for BIOBIT™ FC alone, 84% for BIOBIT™ FC+6% VANISPERSE-CB™, 68% for BIOBIT™ FC+6% CARBOLAZE™ L, and 7% for the untreated control.

Example 10

Comparison to Commercial Products

The procedure described in Example 7 is repeated except 48 BIU/gallon of the *Bacillus thuringiensis* subsp. *kurstaki* spray dried preparation of Example 2 is tank mixed with 0.2% w/w VANISPERSE-CB™ so that 16 BIU are applied at a rate of 20 gallons per acre of surface area. Two commercially available *Bacillus thuringiensis* subsp. *kurstaki* products, Dipel™ 2× WP (Abbott Laboratories) and AGREE™ WP (Ciba-Geigy) are applied in identical formats without the VANISPERSE-CB™.

The results demonstrate that the percent mortality at 3 days after treatment is 53% for *Bacillus thuringiensis* subsp. *kurstaki* preparation plus 0.2% w/w VANISPERSE-CB™, 22% for DIPEL™ 2× WP, 19% for AGREE™ WP, and 0% for the untreated control.

The procedure above is repeated except the active ingredient is applied at a rate of 5 gallons per acre of surface area.

The results indicate that the percent mortality at 3 days after treatment is 99% for the *Bacillus thuringiensis* subsp. *kurstaki* preparation+0.2% w/w VANISPERSE-CB™, 67% for DIPEL™ 2× WP, 39% for AGREE™ WP, and 0% for the untreated control.

Example 11

Comparison of VANISPERSE-CB™ to UVINUL™ P25

VANISPERSE-CB™ is compared to UVINUL™ P25 (para-aminobenzoic acid) using the procedure described in Example 4 except the mixture of the *Bacillus thuringiensis* spray dried preparation and the UV sunscreen is exposed to the sunlamp for 22 hours.

The results for the sunscreens at 0.2% w/w are 79% mortality for VANISPERSE-CB™ and 55% mortality for UVINUL™ P25, while at 0.05% w/w sunscreen, the results are 77% mortality for VANISPERSE-CB™ and 40% mortality for UVINUL™ P25.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A pesticidal composition comprising an amount of a UV sensitive pesticide and a lignin selected from the group consisting of: an oxylignin and a sodium lignosulphonate, as a UV sunscreen in an effective amount to protect the pesticide against inactivation by UV radiation, wherein the lignin has a surface tension of 50–54 dynes/cm (1% aqueous solution), a molecular size of less than 20,000, less than 2.0% sulphonic sulphur as % S on solids, and 0% reducing sugars.

2. The pesticidal composition according to claim 1, wherein the lignin further has a temperature stability of up to 120° C.

3. The pesticidal composition according to claim 1, wherein the lignin further has a salt tolerance of up to 70 ppm.

4. The pesticidal composition according to claim 1, wherein the oxylignin is in the form of a salt selected from the group consisting of Na, K, Ca, Mg, $NH_3$, and Fe.

5. The pesticidal composition according to claim 1, wherein the pesticide is an insecticide, a fungicide, a herbicide, a rodenticide, a molluscicide, a miticide, an ovicide, an algicide, a larvicide, a bactericide, and a nematocide.

6. The pesticidal composition according to claim 1, wherein the pesticide is a Bacillus related pesticide.

7. The pesticidal composition according to claim 6, wherein the Bacillus related pesticide is a *Bacillus thuringiensis* pesticide or spore.

8. The pesticidal composition according to claim 7, wherein the *Bacillus thuringiensis* pesticide is a delta-endotoxin or a pesticidally-active fragment thereof.

9. The pesticidal composition according to claim 8, wherein the delta-endotoxin or the pesticidally-active fragment thereof is obtained from a strain selected from the group consisting of *Bacillus thuringiensis* subsp. *aizawai, Bacillus thuringiensis* subsp. *alesti, Bacillus thuringiensis* subsp. *canadiensis, Bacillus thuringiensis* subsp. *colmeri, Bacillus thuringiensis* subsp. *coreanensis, Bacillus thuringiensis* subsp. *dakota, Bacillus thuringiensis* subsp. *darmstadiensis, Bacillus thuringiensis* subsp. *dendrolimus, Bacillus thuringiensis* subsp. *entomocidus, Bacillus thuringiensis* subsp. *finitimus, Bacillus thuringierlsis* subsp. *galleriae, Bacillus thuringiensis* subsp. *indiana, Bacillus thuringiensis* subsp. *israelensis, Bacillus thuringiensis* subsp. *kenyae, Bacillus thuringiensis* subsp. *kumamotoensis, Bacillus thuringiensis* subsp. *kurstaki, Bacillus thuringiensis* subsp. *kyushuensis, Bacillus thuringiensis* subsp. *japonensis, Bacillus thuringiensis* subsp. *mexcanensis, Bacillus thuringiensis,* subsp. *morrisoni, Bacillus thuringiensis* subsp. *neoleonensis, Bacillus thuringiensis* subsp. *nigeriae, Bacillus thuringiensis* subsp. *ostriniae, Bacillus thuringiensis* subsp. *pakistani, Bacillus thuringiensis* subsp. *pondicheriensis, Bacillus thuringiensis* subsp. *shandongiensis, Bacillus thuringiensis* subsp. *silo, Bacillus thuringiensis* subsp. *sotto, Bacillus thuringiensis* subsp. *subtoxicus, Bacillus thuringiensis* subsp. *tenebrionis, Bacillus thuringiensis* subsp. *thompsoni, Bacillus thuringiensis* subsp. *tochigiensis, Bacillus thuringiensis* subsp. *tohokuensis, Bacillus thuringiensis* subsp. *tolworthi, Bacillus thuringiensis* subsp. *toumanof, Bacillus thuringiensis* subsp. *wuhanensis,* and *Bacillus thuringiensis* subsp. *yunnanensis.*

10. The pesticidal composition according to claim 8, wherein the *Bacillus thuringiensis* delta-endotoxin or the pesticidally-active fragment thereof is selected from the group consisting of CryIA, CryIB, CryIC, CryID, CryIIA, CryIIB, CryIIIA, CryIIIB, CryIIIC, CryIVA, CryIVB, CryIVC, CryIVD, CryV, and CryVI.

11. The pesticidal composition according to claim 8, wherein the delta-endotoxin is a *Bacillus thuringiensis* subsp. *kurstaki* delta-endotoxin or a pesticidally-active fragment thereof.

12. The pesticidal composition according to claim 11, wherein the *Bacillus thuringiensis* subsp. *kurstaki* delta-endotoxin is a CryIA protein or a pesticidally-active fragment thereof.

13. The pesticidal composition according to claim 8, wherein the delta-endotoxin is a *Bacillus thuringiensis* subsp. *aizawai* delta-endotoxin or a pesticidally-active fragment thereof.

14. The pesticidal composition according to claim 13, wherein the *Bacillus thuringiensis* subsp. *aizawai* delta-endotoxin is a CryIC protein or a pesticidally-active fragment thereof.

15. The pesticidal composition according to claim 1, wherein the pesticide is an entomopathogenic virus.

16. The pesticidal composition according to claim 1, wherein the pesticide is an entomopathogenic fungus.

17. The pesticidal composition according to claim 1, wherein the pesticide comprises a chemical pesticide selected from the group consisting of an insecticide, a fungicide, a herbicide, a rodenticide, a molluscicide, a miticide, an ovicide, an algicide, a larvicide, a bactericide, and a nematocide.

18. The pesticidal composition according to claim 17, wherein the chemical insecticide is selected from the group consisting of an insect growth regulator, a carbamate, an organophosphate, a pyrethroid, an inorganic fluorine, a pyrazole, and a pyrrole.

19. The pesticidal composition according to claim 1, wherein the lignin is present in an amount between about 0.001% and about 10% of the volume of pesticide applied to a given target pest.

20. The pesticidal composition according to claim 19, wherein the lignin is present in an amount between about 0.005% and about 8% of the volume of pesticide applied to a given target pest.

21. The pesticidal composition according to claim 20, wherein the lignin is present in an amount between about 0.01% and about 6% of the volume of pesticide applied to a given target pest.

22. The pesticidal composition according to claim 21, wherein the lignin is present in an amount between about 0.02% and about 4% of the volume of pesticide applied to a given target pest.

23. The pesticidal composition according to claim 22, wherein the lignin is present in an amount between about 0.05% and about 2% of the volume of pesticide applied to a given target pest.

24. The pesticidal composition according to claim 1, wherein the lignin is present in an amount between about 1% and about 18% of the weight or volume of the formulation.

25. The pesticidal composition according to claim 24, wherein the lignin is present in an amount between about 1% and about 15% of the weight or volume of the formulation.

26. The pesticidal composition according to claim 25, wherein the lignin is present in an amount between about 1% and about 12% of the weight or volume of the formulation.

27. The pesticidal composition according to claim 26, wherein the lignin is present in an amount between about 1% and about 10% of the weight or volume of the formulation.

28. The pesticidal composition according to claim 27, wherein the lignin is present in an amount between about 1% and about 5% of the weight or the volume of the formulation.

29. The pesticidal composition according to claim 1, wherein the lignin is utilized in a form that is not complexed, crosslinked, or covalently bound to the pesticide.

30. A method for protecting a UV sensitive pesticide against inactivation by UV radiation comprising treating the pesticide with a lignin selected from the group consisting of: an oxylignin and a sodium lignosulphonate, wherein the lignin has a surface tension of 50–54 dynes/cm (1% aqueous solution), a molecular size of less than 20,000, less than 2.0% sulphonic sulphur as % S on solids, and 0% reducing sugars.

31. A method for controlling a pest comprising exposing the pest to a pesticidal composition according to claim 1.

32. A method for controlling a pest comprising applying to a transgenic plant, which contains a gene that encodes a *Bacillus thuringiensis* pesticide, a lignin selected from the group consisting of: an oxylignin and a sodium lignosulphonate, as a UV sunscreen in an effective amount to protect the *Bacillus thuringiensis* pesticide against inactivation by UV radiation, wherein the lignin has a surface tension of 50–54 dynes/cm (1% aqueous solution), a molecular size of less than 20,000, less than 2.0% sulphonic sulphur as % S on solids, and 0% reducing sugars.

* * * * *